U.S. Patent Number: 5,788,668
Date of Patent: Aug. 4, 1998

Leonhardt

[54] VIBRATIONAL ENHANCEMENT OF INTRAVENOUS GAS EXCHANGING DEVICES AND LONG-TERM INTRAVENOUS DEVICES

[75] Inventor: Howard J. Leonhardt, Davie, Fla.

[73] Assignee: World Medical Manufacturing Corporation, Sunrise, Fla.

[21] Appl. No.: 644,001

[22] Filed: May 9, 1996

[51] Int. Cl.$^6$ .................................... A61B 17/22
[52] U.S. Cl. ................................ 604/23; 604/22
[58] Field of Search .................. 604/266, 267, 604/22; 606/169

[56] References Cited

U.S. PATENT DOCUMENTS

| | | | |
|---|---|---|---|
| 4,509,947 | 4/1985 | Lattin | 604/266 |
| 4,583,969 | 4/1986 | Mortenser | 604/4 |
| 4,631,053 | 12/1986 | Teheri | 604/4 |
| 5,271,735 | 12/1993 | Greenfeld et al. | 604/66 |
| 5,336,164 | 8/1994 | Snider et al. | 604/4 |
| 5,342,380 | 8/1994 | Hood | 606/169 |

FOREIGN PATENT DOCUMENTS

| | | |
|---|---|---|
| 95/01752 | 1/1995 | WIPO . |
| 95/09572 | 4/1995 | WIPO . |

Primary Examiner—Manuel Mendez
Attorney, Agent, or Firm—Paul F. Bawel

[57] ABSTRACT

A method whereby a programmable signal source produces a desired output signal which is transferred by a conduit means or conducting means into a patient by percutaneous venous insertion. The output signal is either vibrational or electrical. If vibrational, the conduit means or one or more transducers radiates the output signal into the treatment site within a patient. If electrical, one or more transducers receive the output signal and convert the output signal into vibration and then radiate it into the treatment site within a patient. The treatment site is the location of a catheter or other intravenous device, residing within the patient for the purposes of gas exchange in the blood stream or for other long-term treatment. The presence of the vibration increases the efficiency of intravenous gas exchanging devices significantly, and prevents clot formation on the surface of intravenous devices. The programmable output source includes signal conditioning allowing the output signal to be manipulated so as to best accommodate whatever particular catheter or device is being employed. The increase in efficiency of the catheter or device resulting from the vibration correlates into safer patient treatment and longer life for the catheter or device employed.

15 Claims, 1 Drawing Sheet

VIBRATIONAL ENHANCEMENT OF INTRAVENOUS GAS EXCHANGING DEVICES AND LONG-TERM INTRAVENOUS DEVICES

DEFINITIONS

1. The terms catheter, intracavity or intravenous device, and device are used interchangeably throughout the specification. In use, they may be different items. For the purposes of the disclosed invention, their differences are irrelevant allowing the interchange of terms. When multiple terms are used together within the disclosure, the terms are meant only to remind the reader of the full scope of the application of the invention.

2. Long-term refers to the length of time required before clotting begins because of the presents of an intravenous device or catheter.

BACKGROUND OF THE INVENTION

1. Field of the Invention

This invention relates to improving devices which reside in blood vessels long-term and/or for the purpose of aiding or temporarily replacing the function of the lungs. Namely the present invention increases the efficiency of intravenous gas exchanging and aeration devices, and eliminates clotting on any intravenous device.

2. Description of the Prior Art

A search of prior art revealed only devices which will benefit from this invention. No prior art was found disclosing any device similar or related to the invention disclosed herein. Therefore, this section will describe devices with which the invention will be and may be used.

Catheters are devices inserted into a cavity of a patient's body allowing direct treatment internal to that cavity with limited intrusion into the body. One type of catheter allows vital gas exchange to occur within the body if the lungs can not function properly. Most of these devices have had limited success because the gas exchange provided is not sufficient to sustain the life of the patient by itself. These catheters are difficult and time consuming to manufacture and are accordingly expensive.

One patented catheter disclosed by Snider et. al., U.S. Pat. No. 5,336,164 sustains sufficient oxygen, carbon dioxide and nitrogen transfer in the blood supply to safely sustain life. This catheter has closed-ended hollow fibers on the surface of the main tube in pine needle-like fashion. The catheter is placed in the femoral vein, and is routed through the inferior vena cava, the right atrium, the right ventricle, and into the pulmonary artery. The greatest gas exchange takes place in the right atrium and right ventricle. It claims the ability to fulfill the basal metabolic needs of an adult patient. That is more than sufficient to sustain life for a body at rest. It is manufactured from non-reactive materials and may reside within the patient for several hours or days, depending on the patient's need. It is with this device the inventor tested the present invention. But the advantages of the invention are applicable to any device residing within a patient for an extended period or employed to exchange gasses in the blood. All of these devices have common problems.

Another artificial lung device preceding Snider's device is the Intravascular Oxygenator System disclosed by S. Taheri, U.S. Pat. No. 4,631,053. This device was the first to use pine needle-like hollow fibers extending from a main tube to exchange gasses within the blood stream. It resides within the inferior vena cava. It probably can not supply the minimal basal metabolic needs of an adult patient at rest, and would require some other device to sustain life.

The most significant problem for gas exchanging devices is sufficient gas exchange to safely preserve life by the device itself. Most devices must be supplemented by another source of gas exchange such as Positive Pressure Ventilation, Extracorporeal Oxygenation or the lungs themselves. Mortensen disclosed an intravenous oxygenator (IVOX) in U.S. Pat. No. 4,583,969 which satisfies only forty percent (40%) of the basal metabolic needs of an adult patient under optimal conditions. This device lies only in the inferior vena cava.

External devices such as those which perform extracorpreal membrane oxygenation require multiple incisions into the patient for removing untreated blood from the patient and returning treated blood to the patient. They are not capable of replacing lung function for more than a few hours and their pumping mechanism causes hemolysis. Hemolysis is bruising or damaging the blood cells by compression within the blood pump. The effect to the red blood cells is their decreased capability to carry and distribute oxygen to body tissue, which is obviously undesirable.

Another significant problem for any long term resident catheter is the formation of blood clots on the device. Blood cells diverge from their normal path through the vessel in the vicinity of the intravessel catheter. Along the surface of the catheter exposed to the blood flow occurs a physical phenomenon of fluid dynamics known as slippage, whereby normal flow decreases and actually stops for those cells in contact with the catheter itself. The result is a stagnant area on the surface of the intravenous device, particularly in areas on the body of the device where joints and irregularities occur. Once the stagnant area forms, surface tension forms a boundary which is difficult to penetrate or disrupt. The boundary layer protects the stagnation and eventually leads to clotting.

Clotting occurs because of the nature of blood cells themselves, especially the platelets. Platelets exist at the rate of approximately 250,000 for each cubic centimeter of human blood. Platelet aggregation occurs due to chemical reactions, the discussion of which is not important to this disclosure. What is important is that the chemical reactions, which occur when the blood flow stops, create an environment that facilitates platelet and other blood cell aggregation, which eventually grows into a clot. Once there is a stagnant layer of blood on the catheter surface these chemical reactions begin. The more irregular the catheter, the more likely clots are to form for any given amount of time. The blood flow past the device may dislodge the clot which then travels in the vessel until the clot comes to a vessel through which it can not pass thereby blocking the blood flow. Clots capable of endangering the health of the patient form in as little as one (1) hour. Furthermore, these clots eventually affect the performance of the catheter by plugging orifices resulting in the catheter's replacement.

This description of art is not intended to constitute an admission that any patent, publication or other information referred to is "prior art" with respect to the invention disclosed herein, unless specifically designated as such. Additionally, the preceding section should not be construed to mean that a search has been made or that no other pertinent information as defined in 37 C.F.R. §1.56 exists.

SUMMARY OF THE INVENTION

The inventor conceived the present invention and reduced it to practice with the knowledge of the foregoing. The overall objective of the invention is to extend the capabilities of intracavity devices, primarily those utilized for gas exchange. Included in the overall objective is the benefit from this invention to other types of long-term intracavity devices because use of the invention extends the life of the device by preventing clotting on and around the device. These benefits extend not only to existing devices, but also to future devices and methods yet to be invented or discovered.

The present invention discloses a method for increasing the efficiency of gas exchange for intravenous gas exchanging devices. The present invention further discloses a method for preventing the accumulation of blood cells on catheters and associated devices, residing within the body for sufficient time for clotting to form, thereby positively affecting the safety of the patient and the efficiency of the catheter. The method employs a controllable signal source whose output is conductively coupled to a conduit which transmits and radiates the vibration at the site of a catheter. The vibration facilitates efficient gas exchange and causes blood cell movement where flow has been interrupted along the surface of the catheter.

The result of these embodiments is the prevention of clot formation on the catheter body, and a significant increase in gas exchange efficiency. The inventor performed tests to quantify the effects of vibration on gas exchange with the Snider catheter. The inventor applied a vibration supplied by a vibrational source set to output a constant wave form at a set frequency. The inventor mechanically coupled the output vibrational source to a guide wire. The inventor then varied the amplitude of the vibration until the vibration resonated from the entire length of the guide wire; however, most of the vibrational energy radiated from the guide wire's distal end. Placing the guide wire in a water bath with an operating Snider catheter, the inventor measured the gas exchange capabilities of the catheter with the vibration off, on, and cycled off and on at various time intervals.

Without the vibration present in the water bath, the gas exchanging ability of the Snider catheter was unchanged from all previous testing on the device. With the vibration present in an uncycled state, the gas exchanging ability of the catheter increased immediately by thirty percent (30%), held constant at thirty percent (30%) for one (1) minute, and then decreased to a fifteen percent (15%) efficiency increase of the Snider catheter, which was maintained for however long the vibration remained present in the water bath. When the inventor turned the vibrational source off, the Snider catheter immediately returned to its nominal gas exchange rate. The vibration excites the gas molecules allowing them to more efficiently pass through the porous fibers of the catheter, and allowing oxygen molecules to efficiently attach to red blood cells for transportation to the body.

To overcome the decrease from thirty percent (30%) to fifteen percent (15%) efficiency increase occurring from continuous exposure to a constant vibration, the inventor cycled the vibration on and off for various cycle periods. The inventor found that the thirty percent (30%) increase in efficiency of the Snider catheter is maintainable for an indefinite period if the vibrational source is cycled on and off at approximately one (1) second cycles continuously. Furthermore, efficiency increases below thirty percent (30%) may be maintainable for longer cycle periods with on/off cycle ratio and overall cycle period manipulation. A thirty percent (30%) efficiency increase for the Snider device is sufficient to maintain life in an adult with an oxygen load requirement equal to that of an adult doing heavy exercise. The reasons for the decrease in added efficiency caused by continuous vibrational exposure is unknown.

The vibration, in either a constant or pulsed state, prevents clotting by eliminating slippage, and the formation of a boundary layer near the surface of the catheter and an area of stagnation below. In turn, this prevents an aggregation of platelets and other blood cells necessary for clots to form. The lack of clots eliminates the clogging of orifices on the catheter. These benefits continue as long as the vibration is present.

It is therefore a primary objective of the invention to provide a method which will significantly increase the efficiency of intravascular artificial lungs.

Another primary objective of the invention is to provide a method which will prevent clotting of long-term intravascular devices.

Another objective of the invention is to provide a device to deliver vibration to internal treatment sites along the entire length of the catheter to be benefited.

Another objective of the invention is to disclose a method to deliver vibration to an internal treatment site(s) at one or more single points along the catheter to be benefited. The point radiation is to be delivered in either an omnidirectional or an aimed directional manner.

The disclosed method is all that is claimed and the method does not assert any interests to any device with which this method is utilized:

BRIEF DESCRIPTION OF THE DRAWINGS

In all of the drawings containing a vibrational or signal source, the drawing is representational and any off-the-shelf signal generator combined with the proper signal conditioning equipment may be substituted. The elements represented in the drawings should not be restricted to what is shown, and as such are aids to understanding the method disclosed. It is the combination of these elements, or their equivalents, and the method of their employment which enhances other devices and which is claimed.

DETAILED DESCRIPTION OF THE PREFERRED EMBODIMENTS

Figure 1:
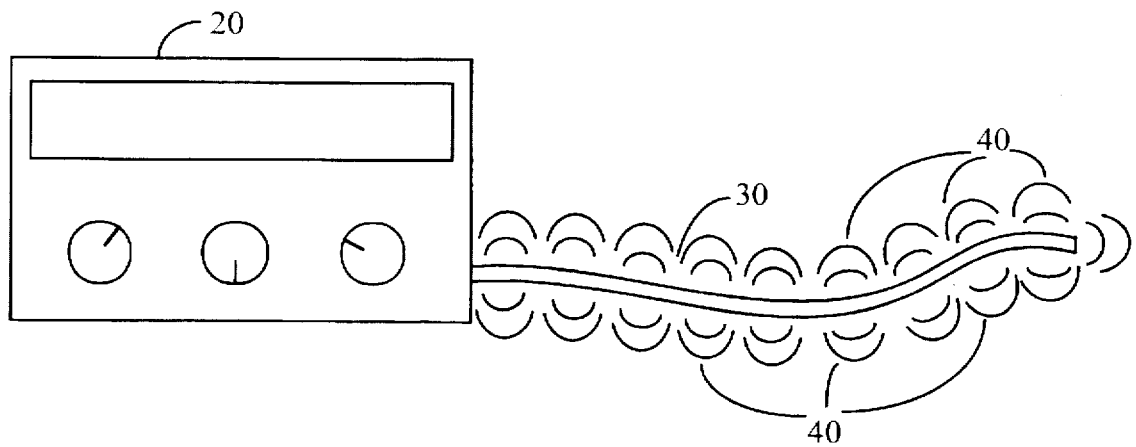
FIG. 1 represents the first embodiment discussed comprising the basic elements necessary to the disclosed invention. In this embodiment the conduit means radiates vibration along its longitudinal axis.

Referring initially to FIG. 1 illustrating the basic embodiment of the invention, note the simplistic nature of the invention. The output vibrational source 20 is vibrationally coupled to the conduit 30. The output vibrational source 20 produces the vibration 40 desired to be radiated at the treatment site, and the conduit 30 conducts the vibration 40 and radiates the vibration 40 into the treatment site. The treatment site itself may be located well within the patient, or the treatment site may be the entire path along which the catheter resides within the patient.

The vibration 40 is selectable as to amplitude and frequency content when the output vibrational source 20 is in either the steady state mode or a programmable variable mode. The output vibrational source 20 also contains signal conditioning allowing the physician or technician to modify the shape of the vibration 40 from a traditional sine wave into various derivatives, such as a saw tooth wave, a square wave, a pulsed signal or otherwise. The output vibrational source 20 may also vary the time content of the vibration 40.

A simple programmable feature allows the physician or technician to select a range of frequencies and/or amplitudes to switch to or sweep across for a set or random time period. Additionally, the signal shape of the vibration 40 may be modified during the time period. This allows the treating physician or technician to setup and adjust the output vibrational source 20 so that the vibration 40 is optimal for the catheter or device used.

For example, perhaps a gas exchange device oxygenates the blood best at one set frequency and amplitude as a sine wave, removes carbon dioxide at another set frequency and amplitude as a sine wave, and prevents clotting best by sweeping the vibration over a frequency range which increases in amplitude with increased frequency as a saw tooth wave. The output vibrational source 20 will accommodate each requirement for a desired time period and repeat the patterns or then generate other selected patterns. Such flexibility allows the invention disclosed herein to accommodate as many devices as possible to their fullest capacity.

The conduit 30 may be the guide wire or some other tool which efficiently accepts the vibration 40, transfers the vibration 40 along the conduit's 30 longitudinal axis, and radiates the vibration 40 in an omnidirectional manner away from the conduit 30 and into the surrounding environment. Guide wires are metal and are therefore naturally disposed to conducting and radiating vibrations, and also are easily positioned within the patient. This combination allows easy use of existing apparatus to employ the inventive method disclosed herein.

The one constraint the conduit 30 has is that it must be capable of insertion into the patient. The insertion of the conduit 30 into the patient may be via one of the lumens in a catheter or along side of a catheter or other device such that the conduit 30, once placed for treatment within the patient, is aligned with the portion of a catheter or device where the gas exchange and/or clotting occurs. It may be desirable to insert the conduit 30 into the patient from a separate insertion point, but this increases the risks associated with any surgical procedure.

The conduit 30 may also be the catheter body itself. The ability of the catheter body to be the conduit 30 depends upon the rigidity of the catheter body, its overall length, and the damping placed upon the catheter body by its entry point into the body. If the catheter body is capable of transmitting and radiating the vibration 40 to the treatment site, the need for an extra lumen or larger insertion point is eliminated. Using the catheter body as the conduit 30 is best suited for the elimination of clotting because only minimal vibration 40 on the surface of a device is necessary to prevent slippage and break down the boundary layer cause by surface tension, and therefore prevent clotting in the blood stream.

Figure 2:
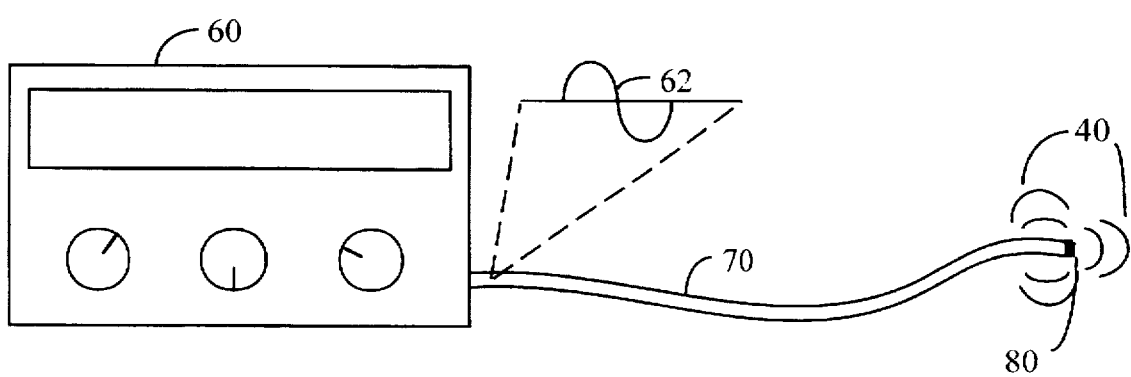
FIG. 2 represents the another embodiment where the output signal is transferred along the conducting means to a transducer which radiates vibration at selected sites.

Another embodiment eliminates the natural damping effect of the patient's body and catheter on the vibrating conduit 30. This embodiment is also effective when the vibration 40 needs to be or must be applied only locally to the treatment site. Referring to FIG. 2, this embodiment utilizes an output signal source 60 capable of complex signal conditioning as described in the previous embodiment. A conducting means 70, coupled to the output signal source, accepts the output signal 62 and transmits it without significant signal degradation to a transducer 80. The output signal 62 may be electrical or vibrational. The conducting means 70 does not itself radiate the vibration 40, but transfers the output signal 62 to a transducer 80 which converts the output signal 62 into vibration 40 and/or radiates the vibration 40 to the desired site for localized treatment. The transducer 80 radiates the vibration 40 in an omnidirectional or directional manner into the treatment site. The vibration 40 thereby increases the efficiency of any gas exchanging device and prevents clotting on the devices.

The conducting means 70 may be any of several known mechanisms for conducting electrical or vibrational signals. If the output signal 62 is electrical, wires may be embedded in the catheter wall allowing the catheter to insulate the output signal and free a lumen for other needs. Wires may reside in a lumen within the catheter. Generally, a transducer requires a signal path wire and a return path wire, and occasionally a separate power wire. There are many types of wire conductors comprising multiple insulated and distinct signal paths mated to each other by the insulating material available for this purpose. The conducting means 70 for an electrical output signal 62 may also be a metal guide wire wherein the guide wire provides the signal path. The return path may then be the patient himself or herself, or a separate insulated wire running in or along the catheter.

For an electrical output signal 62, multiple transducers 80 are electrically isolated from each other. The transducer(s) 80 are mounted on or embedded in the catheter such that the catheter does not dampen the vibration 40 once produced by the transducer(s) 80. The transducer(s) 80 may be directional or omnidirectional as needed.

If the output signal 62 is vibrational, the conducting means 70 may be a specially manufactured guide wire capable of transferring the vibration to the transducer without radiating the output signal 62 along itself. The body of the guide wire may be vibrationally insulated to direct the output signal 62 down the conducting means 70 to one or more transducers 80. The one or more transducers 80 may be built into the guide wire or mounted externally on the guide wire and conductively coupled to the output signal 62.

The guide wire itself may serve as the transducer 80 by having nonhomogeneous surfaces and/or areas manufactured or machined into the guide wire made of homogeneous material. These nonhomogeneous surfaces and/or areas create a discontinuity which disrupts the flow of the output signal 62 and causes the vibration 40 to radiate at that point. These nonhomogeneous surfaces and/or areas may radiate the vibration 40 either in a preferred direction or omnidirectionally. Rotation of the guide wire thereby allows the physician or technician to aim the directional transducer 80. Radiopaque material marking the location of directional transducers 80 on the guide wire aid in this operation.

A vibrational output signal 62 may utilize a conducting means 70 of fluid column since fluids are essentially non-compressible. The fluid may be contained within a lumen of the catheter which accepts the output signal 62 at the proximal end of the catheter and transmits the output signal 62 to the sealed distal end of the catheter for radiation by a transducer 80. Since the walls of a lumen are generally smooth, most of the energy is transferred to the distal end of the lumen. A separate fluid filled tube may also be inserted into the patient via a residing catheter or otherwise for use as the conducting means 70. A fluid column works best with gentle curves and is defeated if the lumen kinks thereby blocking the path for the output signal 62.

At the distal end of the fluid column conducting means 70 resides a transducer 80. The transducer 80 is a vibrationally transparent material which seals the end of the conducting means 70 such that the fluid within creates a closed system requiring the transfer of the output signal 62 along the entire length of the conducting means 70. When the output signal 62 reaches the transducer 80, the output signal 62 causes the transducer 80 to pulsate proportional to the output signal 62, thereby radiating the desired vibration 40 into the treatment site.

The preceding specific embodiments are representative and illustrative of the practice of the invention. It is to be understood by all that other configurations employing these basic elements may be employed without departing from the spirit of the invention or the scope of the claims.

What I claim is:

1. A device for increasing the efficiency of a gas exchanging or long-term intravenous catheter, said device comprising:

an output vibrational source having controllable signal conditioning capabilities, an output vibration emitting from said output vibrational source; and a conduit means vibrationally coupled to said source for accepting, transferring and radiating said output vibration along the intracavity path of said conduit means; wherein said output vibration performs one of the functions of enhancing gas exchange between said catheter and a blood stream, and preventing the formation of blood clots on said catheter; and said radiation of said output vibration generally occurs along the length of said conduit means.

2. The device of claim 1 wherein said conduit means is the catheter body of said catheter.

3. A device for increasing the efficiency of a gas exchanging or long-term intravenous catheter, said device comprising:

an output signal source having controllable signal conditioning capabilities;

an output signal emitting from said output signal source;

a conducting means coupled to said source for transmitting said output signal to a treatment site;

one or more transducers near said treatment site; each of said transducers having an input conductively coupled to said conducting means; each of said transducers capable of converting said output signal into a vibrational representation of said output signal, and capable of radiating said vibrational representation.

4. The device of claim 3 wherein the conducting means are electrical conductors.

5. The device of claim 3 wherein the conducting means is a guide wire.

6. The device of claim 3 wherein the conducting means is a fluid filled column.

7. The device of claim 5 wherein said transducers are nonhomogeneous areas within said guide wire.

8. A method for increasing the efficiency of a gas exchanging or long-term intravenous catheter, said method comprising the steps:

placing a conducting means in the proximity of said catheter;

generating a signal with a signal source;

coupling said signal to said conducting means;

transferring said signal along said conducting means;

radiating said signal from at least one point on said conducting means; and maintaining said radiation of said signal for a predetermined period of time.

9. The method of claim 8, wherein said predetermined period is generally continuous during the time said catheter resides within a patient.

10. The method of claim 8, wherein said predetermined period of time is created by cycling said vibration on and off.

11. The method of claim 8, wherein said point on said conducting means is a transducer.

12. The method of claim 8, wherein said radiated signal radiates from substantially all points on said conducting means along said catheter.

13. The device of claim 1, wherein said vibration is cycled on and off.

14. The device of claim 1 wherein said conduit means is a transducer for radiating said output vibration.

15. The device of claim 3, wherein said predetermined period of time is created by cycling said vibration on and off.

* * * * *